(12) United States Patent
Pazanowski et al.

(10) Patent No.: US 8,388,664 B2
(45) Date of Patent: Mar. 5, 2013

(54) LOW PROFILE IMPLANT LOCKING PLATES

(76) Inventors: Walt Pazanowski, Cardiff, CA (US);
Laurence M. McKinley, Escondido, CA (US); Timothy Allen Peppers, LaJolla, CA (US)

( * ) Notice: Subject to any disclaimer, the term of this patent is extended or adjusted under 35 U.S.C. 154(b) by 822 days.

(21) Appl. No.: 12/353,845

(22) Filed: Jan. 14, 2009

(65) Prior Publication Data

US 2009/0254127 A1 Oct. 8, 2009

Related U.S. Application Data

(60) Provisional application No. 61/020,864, filed on Jan. 14, 2008.

(51) Int. Cl.
*A61B 17/80* (2006.01)

(52) U.S. Cl. .......... 606/286; 606/279; 606/246

(58) Field of Classification Search .......... 606/246, 606/263, 279, 283, 284, 286
See application file for complete search history.

(56) References Cited

U.S. PATENT DOCUMENTS

| 2004/0153078 A1* | 8/2004 | Grinberg ............ 606/75 |
| 2005/0154390 A1* | 7/2005 | Biedermann et al. ...... 606/61 |

* cited by examiner

*Primary Examiner* — Cris L Rodriguez
*Assistant Examiner* — Eric Rosen
(74) *Attorney, Agent, or Firm* — Kauth, Pomeroy, Peck & Bailey LLP

(57) ABSTRACT

An implant locking plate system and a method of using such a system are provided. The implant locking plate system generally includes at least one "T"-headed bone anchor, such as a screw or bolt that can be inserted into a vertebral body adjacent to the artificial disc to be stabilized, and a stabilizing plate attached to the bone anchor designed to overlap at least a portion of the artificial disk or graft when the bone anchor is inserted into the vertebral body adjacent to the artificial disk or graft.

23 Claims, 3 Drawing Sheets

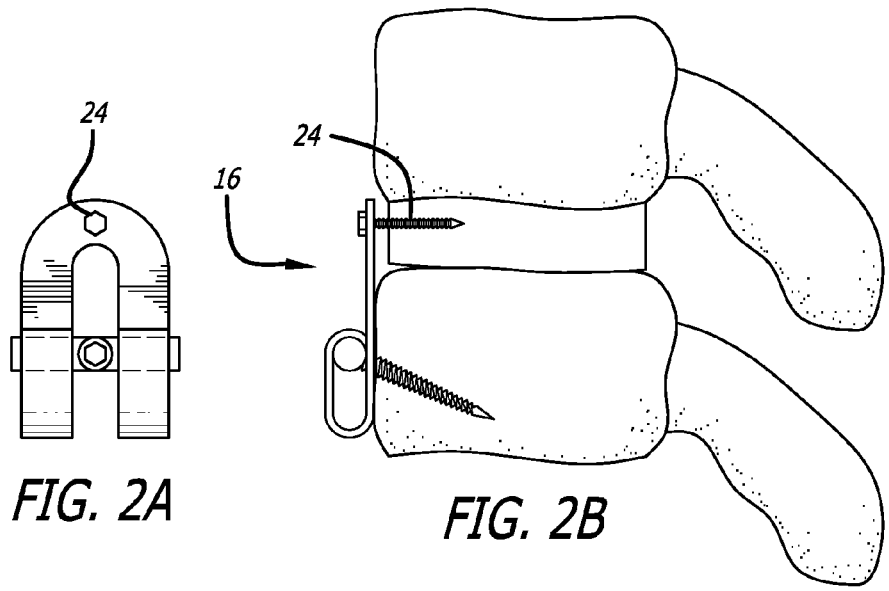
FIG. 2A
FIG. 2B
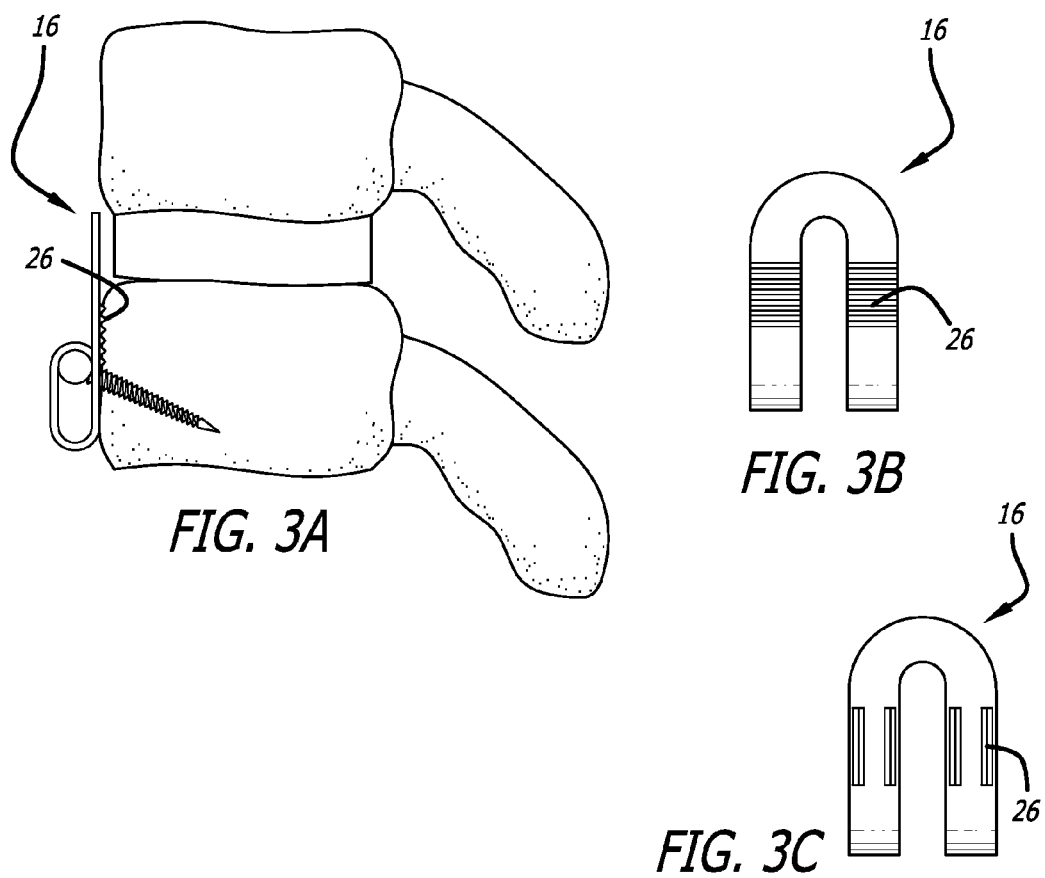
FIG. 3A
FIG. 3B
FIG. 3C

LOW PROFILE IMPLANT LOCKING PLATES

CROSS-REFERENCE TO RELATED APPLICATIONS

The current application claims priority to U.S. Provisional Application No. 61/020,864, filed Jan. 14, 2008, the disclosure of which is incorporated herein by reference.

FIELD OF THE INVENTION

The current invention is directed to an implant locking plate; and particularly to low profile adjustable implant locking buttress and fusion plates.

BACKGROUND OF THE INVENTION

Intervertebral discs are fibrous cartilage pads that allow the spine to bend and serve as "shock" absorbers for the vertebrae, absorbing pressure delivered to the spinal column. Additionally, they maintain the proper anatomical separation between two adjacent vertebras. This separation is necessary for allowing nerves to exit and enter unimpeded from the spinal column.

To alleviate the pain caused by a damaged disc, current treatment methods include a discectomy in which the affected intervertebral disc is removed and an interbody fusion implant is inserted. Thereafter, the two adjacent vertebral bodies can be fused together in a process commonly referred to as spinal fusion. The disc prosthesis restores the angular relationship between the adjacent vertebrae to be fused, and provides the material for bone growth to occur between the two vertebral bodies.

A large number of these interbody fusion implants have been developed. These implants act as artificial intervertebral discs and can include fusion cages made from metals and/or synthetic materials. Many prostheses can also be fashioned from allograft bone that is harvested from portions of long bone including the femur, humerus, tibia, fibula, ulna and radius.

Although the success or failure of the fusion can often depend upon the type and properties of the prosthesis that is placed between the adjacent vertebral bodies, the prosthesis must also remain fixed in the desired position so that the appropriate spacing and geometry of the spine can be maintained. Unfortunately, because of the continuous forces that act upon the vertebrae and especially the disc prosthesis there is a tendency for the prosthesis to migrate due to shifting, rotation or slippage. Obviously, such movement can result in pain to the patient and failure of the bone fusion.

To address this risk buttress staples have been developed to help hold the disk prosthesis in place. An example of the current state of the art in this field is disclosed in U.S. Pat. No. 7,341,591, the disclosure of which is incorporated herein by reference. Although these devices have had some success in mitigating the risk of disc slippage, they are relatively difficult to implant in a surgical setting, and rely almost entirely on the integrity of bone screws for stability. Accordingly, a need exists for a graft locking plate that provides greater ease of use and stability.

SUMMARY OF THE INVENTION

The invention is directed to a plate system designed to lock an implant, such as a prosthetic disc or graft, into place on the anterior or posterior portions of the spine. The plate system includes a bone anchor having a "T"-shape head, an elongated threaded shaft extending from the head region to a distal end of the bone anchor screw, and a plate having proximal and distal ends and configured to stabilize the position of the implant. The plate is designed to have a locking configuration where the plate is moved relative to the bone anchor such that one portion of the plate abuts against the implant and a second portion of the plate abuts against the vertebral body to prevent the further rotation of the plate thereby fixing the implant into position.

In one embodiment, the plate includes at least two slotted armatures that interconnect in a rotatable and sliding relation with laterally opposing sides of the T-shaped head region of the bone anchor screw. In one such embodiment, at least one of the armatures includes a locking mechanism, such as a ratchet, a set-screw or a friction fitting designed to prevent further movement of the plate relative to the T-head screw when the plate is placed in the locking configuration.

In another embodiment, the plate further includes an elongated body dimensioned such that it at least partially overlaps the implant when the bone anchor screw is positioned in an adjacent bone. In such an embodiment, the elongated body may be formed as a solid or hollow plate.

In yet another embodiment, the surface of the plate abutting one or both of the vertebral body and graft further includes a plurality of surface features designed to provide additional engagement with the surface of said vertebral body and graft. In one such embodiment the surface features are selected from the group consisting of grooves, ridges, spikes, teeth and bumps. In another such embodiment, the surface features may either run transverse or axial to the longitudinal axis of the plate.

In still another embodiment, the plate may be bent or curved to better conform with the shape of the spine or implant. In one such embodiment, the plate may be bent or curved with respect to either the longitudinal or transverse axis of the plate.

In still yet another embodiment, the elongated body includes a graft anchor for fixation in said graft. In such an embodiment, the graft anchor may be selected from the group consisting of a screw, bolt or spike.

In still yet another embodiment, the elongated body includes a cover portion disposed to at least partially overlap the head of the bone anchor screw to prevent back-out of the bone screw when the plate is in the locked configuration.

In still yet another embodiment, the elongated body is dimensioned such that the distal end of the elongated body overlaps at least a portion of the adjacent vertebral body. In such an embodiment, the plate may include a second bone anchor screw positioned at the distal end of the elongated body such that the screw may be inserted into the adjacent vertebral body. In one such embodiment the second screw is a conventional bone screw. In another embodiment, the second screw has a T-shaped head region and the distal end of the plate is interconnected in a rotatable and sliding relation to the second T-headed screw.

The invention is also directed to methods of stabilizing the spine and locking an implant in place using the plate system of the invention.

BRIEF DESCRIPTION OF THE DRAWINGS

The description will be more fully understood with reference to the following figures, which are presented as exemplary embodiments of the invention and should not be construed as a complete recitation of the scope of the invention, wherein:

FIGS. 2a and 2b show side and top views of an implant locking buttress plate in accordance with another exemplary embodiment of the current invention in which the plates incorporate an implant anchor screw;

FIGS. 3a to 3c show side and top views of yet another embodiment of the implant locking buttress plate in accordance with the current invention in which the plates incorporate bone gripping features;

DETAILED DESCRIPTION OF THE INVENTION

In an anterior lumbar spinal surgery it is often common to insert an implant, such as an artificial disc or bone graft, into a collapsed disc space to reestablish the spacing and curvature of the spine. However, when a patient begins to move and the effects of gravity begin to assert itself on the bone graft it can slip forward and "fall out" of the disc space. The current invention provides a system of implant locking plates that may be anteriorly secured to a vertebral body to stabilize the bone graft and ensure that it cannot slip out of the disc space.

Specifically, the current invention is directed to an implant locking plate system that generally includes at least one "T"-headed bone anchoring means, such as a screw or bolt, that can be inserted into a vertebral body adjacent to the artificial disc to be stabilized, and a stabilizing plate attached to the bone anchoring means designed to overlap at least a portion of the artificial disk or graft when the bone anchor is inserted into the vertebral body adjacent to the artificial disk or graft. Although the stabilizing plate of the current invention may be shaped and dimensioned in any manner suitable for locking the implant into place, one feature of the plate is that it is moveable about the head of the bone anchoring means such that it may be placed into a first unlocked position while the bone anchoring means is inserted into the vertebral body, and a second locked position once the bone anchoring means is fully inserted into the vertebral body. The ability to change the conformation of the plate relative to the bone anchor allows for easy access to the bone anchoring means and easy placement and adjustment of the plate during insertion, and a fixation mechanism independent of the bone anchor when the plate is in its final locked position to better stabilize the implant.

Figure 1A:
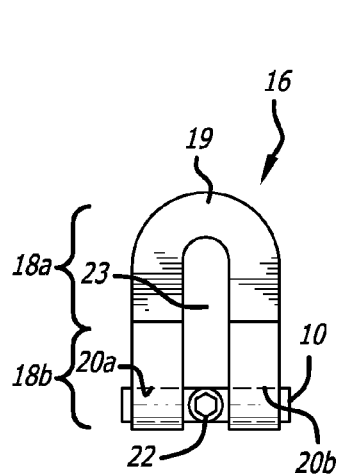
FIGS. 1a to 1d show side and top views of a graft locking buttress plate in accordance with an exemplary embodiment of the current invention in both unlocked (1a and 1b) and locked (1c and 1d) configurations.
Figure 1B:
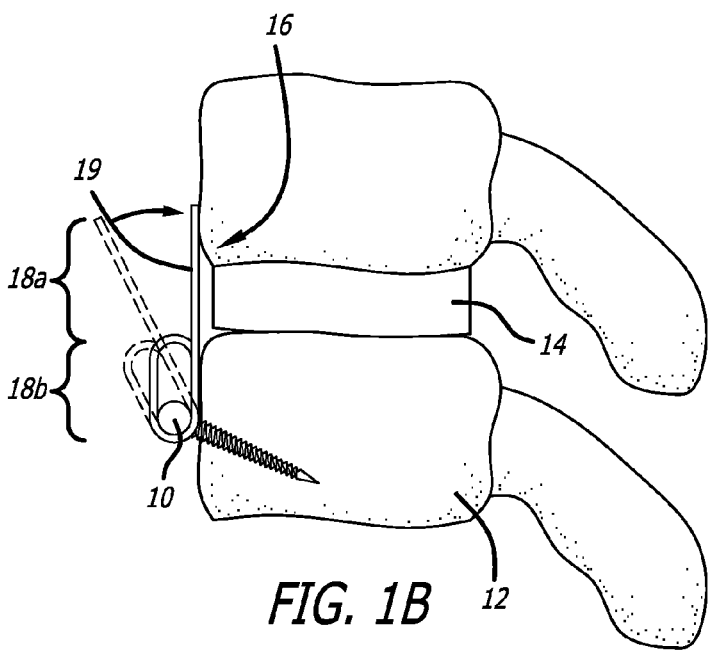
Figure 1C:
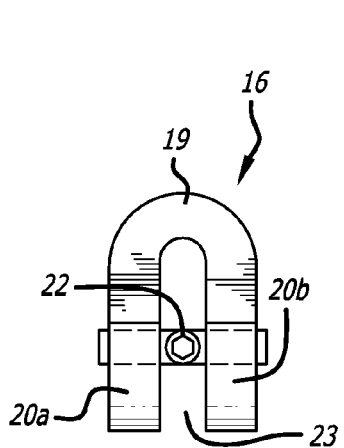
Figure 1D:
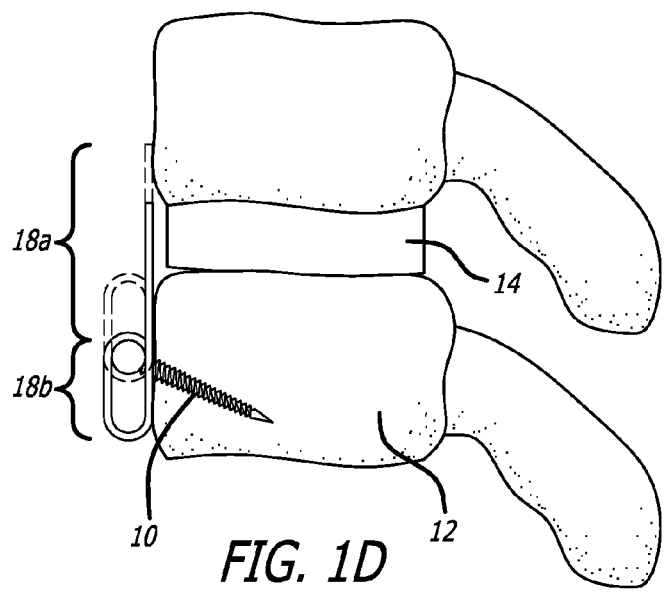

An exemplary embodiment of the implant locking plate of the current invention is illustrated in FIGS. 1a and 1b. As shown, the device generally comprises a "T"-headed screw or bolt (10) that can be inserted into a vertebral body (12) adjacent to the implant site (14). The screw has a plate (16) attached thereto that at least partially overlaps the implant. The plate can pivot and slide around the "T" shaped head such that after the screw is tightened into the vertebral body the plate can then be rotated into place over the bone graft such that the plate rests against the implant to lock it into place (FIG. 1a). The plate itself is formed of two basic portions, an implant locking portion (18a) designed to overlap and stabilize that implant, and a plate locking portion (18b) designed to move about the head of the screw and into a locking position in which the plate is stabilized against further rotation and movement at least by its abutment against the vertebral body.

Specifically, as shown in FIGS. 1a and 1b, the implant-locking portion (18a) comprises an elongated armature (19) that in the exemplary embodiment takes the shape of a solid loop of metal. However, any shape suitable for stabilizing the implant into position may be used, such as, for example, a solid plate. In addition, this portion of the plate can also be shaped to conform to the contours of the spinal column. In one embodiment the plate is formed from a loop of metal, as shown in FIGS. 1a and 1b. Such a hollow centered armature is advantageous because it can be easily bent and/or curved with respect to both a longitudinal and a transverse axis thereof. By allowing these adjustments the contour of the plate may be made to closely match the curves of the spinal column and provide a better fit once implanted.

The locking portion (18b) of the plate generally comprises two retaining arms (20a and 20b) designed to retain the head (22) of the screw (10) and allow for rotation of the plate in a vertical arc about the head of the screw. The two retaining arms also define an elongate slot (23) therebetween through which the shaft of the bone anchor means is positioned and along which the head of the bone anchor means may slide. During operation, once the plate is rotated into position against the implant (shown in FIG. 1a), it may be slid proximally along the slot to lock the locking portion of the plate into place against the vertebral body (shown in FIG. 1b). As shown, in this locked position the rotation of the plate away from the graft is prevented because the locking portion of the plate abuts against the vertebral body.

Although not shown in FIGS. 1a and 1b, it should be understood that an additional locking mechanism may be incorporated into the plate to prevent further movement of the plate once placed into the locked position, and in particular to prevent the locking portion of the plate from sliding out of the locked position. These additional locking mechanisms may take a number of different forms, including mechanical locks, such as, for example, one-way ratchets, set screws or friction fittings. In a preferred embodiment, as shown in FIGS. 2a and 2b, the plate can be provided with a further implant anchoring screw (24) positioned in the graft locking portion of the plate that can be tightened into the implant to provide additional stability. Not only does the implant attachment screw stabilize the plate in position over the implant, but because a portion of the plate overlaps the vertebral body the plate is no longer able to rotate up and away from the implant providing even better stabilization.

In addition to the stabilization provided by the integrated "T"-headed bone anchor and movable graft locking plate, the plate of the current invention may also be provided with further structures to prevent movement of and enhance the stability of the plate, and particularly the ability of the plate to remain in place relative to the implant. Several alternative embodiments showing different locking mechanisms are provided in FIGS. 3a to 3c. As shown, groves or raised ridges (26) may be formed on the underside of the plate (16) such that when the plate is locked into position against the vertebral body the grooves/ridges cut into the bone and/or implant providing additional stability against further movement of the plate, and particularly against rotation or back-out of the plate that would lead to loss of contact with the implant.

Specifically, FIGS. 3a and 3b show a plate having grooves running transverse to the longitudinal axis of the plate formed on the bottom surface of the plate. FIG. 3c shows another alternative having longitudinal grooves that again provide further stability to prevent any rotation of the plate relative to the screw. Although several groove/ridge embodiments are provided, it should be understood that alternative groove/ridge configurations may be used, including, for example, diagonal or saw-toothed grooves/ridges. In addition, the stabilizing features need not be formed as continuous ridges or grooves, but may instead be formed as individual raised features, such as, for example, teeth, bumps or grids. Any such shape or conformation of features may be used such that the plate is provided with an enhanced ability to lock onto the bone of the vertebral body and thereby prevent any movement such as rotation or back-out of the plate relative to the implant.

Figure 4:
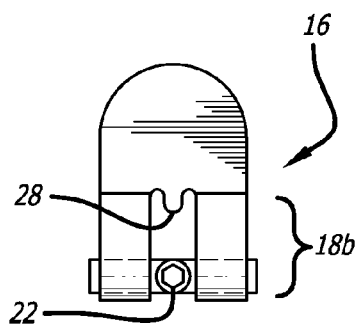
FIG. 4 shows a top view of still another embodiment of the implant locking buttress plate in accordance with the current invention in which the plates incorporate a vertebral anchor locking cover.

Another optional feature of the implant locking plate of the current invention is shown in FIG. 4. In this embodiment, the slidable locking portion (18b) of the plate (16) further incorporates a protrusion (28) that serves to provide an additional buttress surface against the vertebral body, and is also disposed such that when the plate is in the locked position the protrusion overlaps the head of bone anchoring means (22). By overlapping the head of the bone anchoring means, this embodiment of the locking plate further prevents the bone-anchoring screw from backing-out of the vertebral body. Although one embodiment of such a bone anchor cover is described above, it should be understood that any size and shape cover may be used so long as it overlaps at least a portion of the head of the underlying bone anchor means.

Figure 5A:
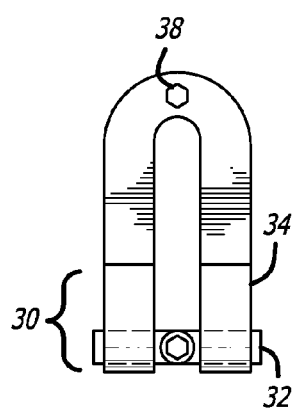
FIGS. 5a and 5b show side and top views of an implant Locking fusion plate in accordance with another exemplary embodiment of the current invention.
Figure 5B:
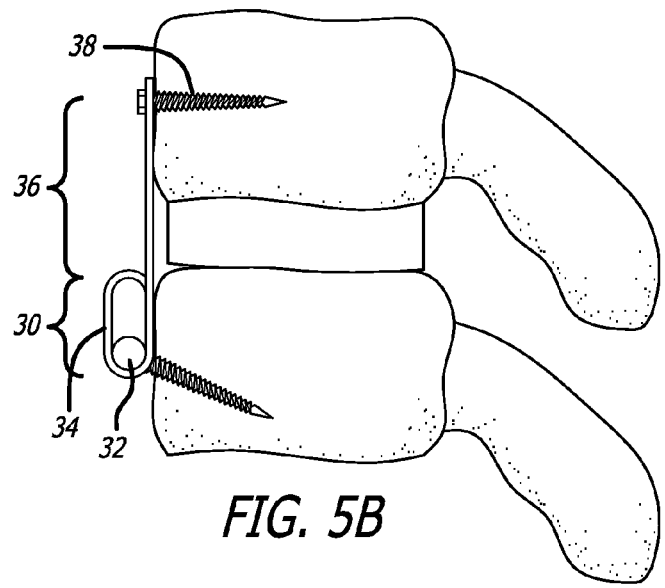

Although the above discussion has focused on implant locking plates designed to be attached to a single vertebral body in an anterior position, it should be understood that plates in accordance with the current invention may also be designed for use as posterior fusion plates, that is to be attached between two vertebral bodies and span the entire disk space, as shown, for example, in FIGS. 5a and 5b. In this embodiment, at least one side of the plate (30) has the "T"-headed bone anchor (32) and locking portion (34) as described above; however, the other side of the plate (36) includes a second bone anchor (38). In such an embodiment, the locking portion of the plate (30) would be inserted first and locked into place, as described above with reference to FIGS. 1 and 2. Then the second bone anchor (38) would be fixed in place. As shown, in this embodiment, the second bone anchor comprises a conventional bone anchor screw or bolt.

Figure 6A:
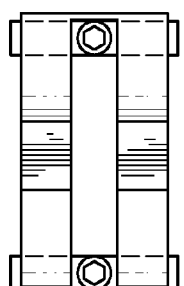
FIGS. 6a and 6b show side and top views of an implant locking fusion plate in accordance with another exemplary embodiment of the current invention.
Figure 6B:
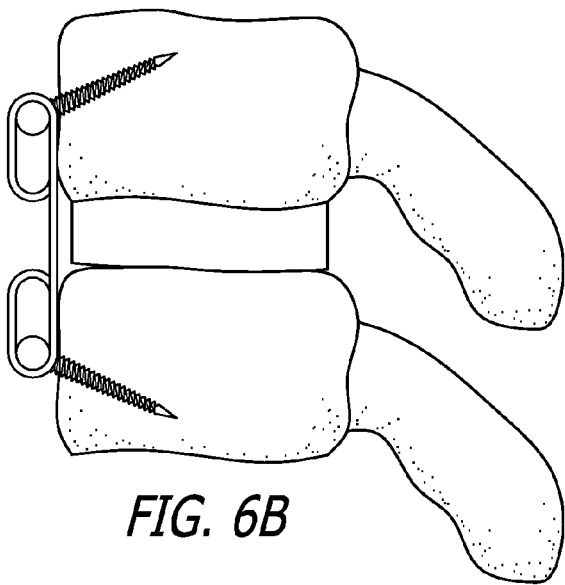

Alternatively, as shown in FIGS. 6a and 6b, both sides of the plate may be slidably interconnected with a separate "T"-headed bone anchor to allow greater flexibility in positioning the plate on both vertebral bodies. In such an embodiment the second of the locking portions would need to be locked into place prior to fully fixing the second bone anchor in position.

It is contemplated that the components of the graft locking plate system of the present invention can be formed from any suitable biocompatible material, including metals such as titanium and titanium alloys. It is further contemplated that the implant locking plate system of the present invention can be used with a variety of prostheses in a number of different applications. In fact, the present system has applicability for any implant system where reinforcement of the implant may be desired.

Finally, it should be understood that the figures provided are only exemplary, and that plates formed in accordance with the current invention may be dimensioned for use on any region of the spine from the cervical to lumbar. Moreover, as discussed above, the plates may also be dimensioned to provide fixation in either anterior or posterior positions.

The above discussion has focused on the design and structure of the plate system itself, it should be understood that the current invention is also directed to methods of stabilizing spinal implants using the plate system of the current invention. In one exemplary method, an implant would be inserted into a disk space and then the implant stabilizing plate system of the current invention would be inserted on the anterior side of the spine to buttress or stabilize the implant in place. Once this stabilizing plate is in position the patient could be turned and either a standard fusion plate, or a fusion plate in accordance with the current invention can be attached on the posterior side of the spine between the vertebral bodies bordering the implant. Accordingly, the implant stabilizing plate system of the current invention can be used with conventional fusion plates or with the fusion plates described herein. Alternatively, the implant stabilizing plate could be inserted where no further fusion is required, or the fusion plate of the current invention could be used in cooperation with a conventional implant buttress plate.

Although specific embodiments of the implant stabilizing plate system of the current invention are described herein, it is expected that persons skilled in the art can and will design alternative embodiments of the buttress plate that are within the scope of the above description either literally or under the Doctrine of Equivalents.

What is claimed is:

1. An implant locking plate system for preventing the migration of an implant, comprising:
   a bone anchor screw configured to be inserted into bone, the bone anchor screw having a T-shaped head region at a proximal end, the T-shaped head region comprising two oppositionally disposed screw armatures extending radically outward from the central axis of the screw, and an elongated threaded shaft extending from the head region to a distal end of the bone anchor screw;
   a plate having proximal and distal ends and configured to stabilize the position of the implant, the plate including:
      a bone anchor screw retaining region at its proximal end having at least two plate armatures defining independent slots, each of said slots disposed along the longitudinal axis of the plate and being interconnected in a rotatable and sliding relation with one of the screw armatures of the T-shaped head region of said bone anchor screw, such that the plate may rotate azimuthally about the T-shaped head region of the screw, and such that the screw armatures may slide within the slots along the longitudinal axis of the plate, and
      the plate further including an elongated body at its distal end attached to said bone anchor screw retaining region and being dimensioned such that the elongated body at least partially overlaps the implant when the bone anchor screw is inserted into an adjacent bone; and
   the plate configured to have a locking configuration where the plate is rotated about the screw armatures of the screw head such that the elongated body abuts against the implant, and where the T-shaped head region of the screw is slidably disposed at the distal end of the plate armature slots in the retaining region of the plate, wherein in said locking configuration the retaining region abuts the adjacent bone and prevents further rotation of the plate such that the elongated body is fixed against the implant.

2. The plate system of claim 1, wherein the elongated body comprises a solid plate.

3. The plate system of claim 1, wherein the elongated body comprises a plate having a central opening therein.

4. The plate system of claim 1, wherein at least one of the at least two plate armatures of the retaining region further comprises a locking mechanism designed to prevent further movement of the plate relative to the bone anchor screw, said locking mechanism being engaged when the plate is placed in the locking configuration.

5. The plate system of claim 4, wherein the locking mechanism is selected from the group consisting of a ratchet, a set-screw and a friction fitting.

6. The plate system of claim 1, wherein at least a portion of a surface of the plate configured for abutting one or both of the adjacent body and implant further includes a plurality of surface features, said surface features being designed to provide additional engagement with the one or both of the adjacent bone and implant.

7. The plate system of claim 6, wherein the surface features are selected from the group consisting of grooves, ridges, spikes, teeth and bumps.

8. The plate system of claim 6, wherein the surface features run transverse to the longitudinal axis of the plate.

9. The plate system of claim 6, wherein the surface features run axial to the longitudinal axis of the plate.

10. The plate system of claim 1, wherein the plate may be bent with respect to a longitudinal axis thereof.

11. The plate system of claim 1, wherein the plate may be curved with respect to a transverse axis thereof.

12. The plate system of claim 1, wherein the elongated body further comprises an implant anchor for fixation in said implant.

13. The plate system of claim 12, wherein the implant anchor is selected from the group consisting of a screw, bolt and spike.

14. The plate system of claim 1, wherein the retaining region further comprises a cover portion disposed to at least partially overlap the head region of the bone anchor screw when said plate is in the locking configuration.

15. The plate system of claim 1, wherein the elongated body is dimensioned such that the distal end of the elongated body overlaps at least a portion of a second adjacent bone.

16. The plate system of claim 15, wherein the elongated body further comprises a second bone anchor screw positioned at the distal end thereof such that the screw may be inserted into the second adjacent bone.

17. The plate system of claim 16, wherein the second screw is a round-headed bone screw.

18. The plate system of claim 16, wherein the second screw has a T-shaped head region comprising two opposed second screw armatures extending radically outward from the central axis of the second screw, and wherein the distal end of the plate includes a second bone anchor screw retaining region.

19. The plate system of claim 16, wherein the first and second bone anchor screws are one of either a screw or a bolt.

20. An implant locking fusion plate system for preventing the migration of an implant, comprising:
a first bone anchor screw configured to be inserted into bone, the first bone anchor screw having a T-shaped head region at a proximal end, the T-shaped head region comprising two oppositionally disposed screw armatures extending radically outward from the central axis of the screw, and an elongated threaded shaft extending from the head region to a distal end of the first bone anchor screw;
a plate having proximal and distal ends and configured to stabilize the position of the implant, the plate including:
a first bone anchor screw retaining region at its proximal end having at least two plate armatures defining independent slots, each of said slots disposed along the longitudinal axis of the plate and being interconnected in a rotatable and sliding relation with one of the screw armatures of the T-shaped head region of said first bone anchor screw, such that the plate may rotate azimuthally about the T-shaped head region of the first screw, and such that the screw armatures may slide within the slots along the longitudinal axis of the plate, and
the plate further including an elongated body at its distal end attached to said first bone anchor screw retaining region and being dimensioned such that the elongated body at least partially overlaps an adjacent vertebral body when the first bone anchor screw is inserted into a first vertebral body;
a second bone anchor screw positioned at the distal end of said elongated body such that the second screw may be inserted into the adjacent vertebral body thereby fixing the elongated body into position; and
the plate configured to have a locking configuration where the plate is rotated about the screw armatures of the screw head such that the elonged body abuts against the implant, and where the T-shaped head region of the first bone anchor screw is slidabliy disposed at the distal end of the plate armature slots in the retaining region of the plate, wherein in said locking configuration the retaining region abuts the first vertebral body and prevents further rotation of the plate such that the elongated body is fixed against the implant.

21. The plate system of claim 20, wherein the second screw is a round-headed bone screw.

22. The plate system of claim 20, wherein the second screw has a T-shaped head region comprising two opposed second screw armatures extending radically outward from the central axis of the second screw, and wherein the distal end of the plate includes a second bone anchor screw retaining region such that the distal end of the plate is interconnected in a rotatable and sliding relation with the two opposed second screw armatures.

23. A method of fixing an implant in place comprising attaching a plate system of claim 1 into place onto a vertebral body adjacent to the implant such that at least a portion of the plate system overlaps and fixes the implant into position within a desired disc space.

* * * * *